(12) United States Patent
Chen et al.

(10) Patent No.: US 12,318,421 B2
(45) Date of Patent: Jun. 3, 2025

(54) MUNG BEAN HULL EXTRACT WITH ANTIVIRAL EFFECT AND EXTRACTION METHOD THEREOF

(71) Applicants: KING'S GROUND BIOTECH CO., LTD., Neipu Township (TW); Hui-Wen Chen, Taipei (TW)

(72) Inventors: Hui-Wen Chen, Taipei (TW); Feng-Ling Yu, Neipu Township (TW); Ying-Nien Hung, Neipu Township (TW); Chia-Chen Pi, Neipu Township (TW)

(73) Assignee: King's Ground Biotech Co., Ltd., Pingtung County (TW)

( * ) Notice: Subject to any disclaimer, the term of this patent is extended or adjusted under 35 U.S.C. 154(b) by 0 days.

(21) Appl. No.: 18/746,153

(22) Filed: Jun. 18, 2024

(65) Prior Publication Data

US 2024/0335493 A1 Oct. 10, 2024

Related U.S. Application Data

(63) Continuation of application No. 17/058,432, filed on Nov. 24, 2020, now abandoned.

(51) Int. Cl.
*A61K 36/48* (2006.01)
*A61K 31/352* (2006.01)
*A61P 31/16* (2006.01)

(52) U.S. Cl.
CPC ............ *A61K 36/48* (2013.01); *A61K 31/352* (2013.01); *A61P 31/16* (2018.01); *A61K 2236/31* (2013.01); *A61K 2236/333* (2013.01); *A61K 2236/51* (2013.01)

(58) Field of Classification Search
None
See application file for complete search history.

(56) References Cited

FOREIGN PATENT DOCUMENTS

CN 107224467 * 10/2017

* cited by examiner

*Primary Examiner* — Michael V Meller
(74) *Attorney, Agent, or Firm* — BACON & THOMAS, PLLC (57) ABSTRACT

The present invention is a mung bean hull extract with antiviral effect, and the mung bean hull extract achieves antiviral effect by inhibiting α-glucosidase and neuraminidase. The present invention also relates to a method for extracting the mung bean hull extract with antiviral effect and applications of the extract obtained by the method.

3 Claims, 13 Drawing Sheets

MUNG BEAN HULL EXTRACT WITH ANTIVIRAL EFFECT AND EXTRACTION METHOD THEREOF

CROSS-REFERENCE TO RELATED APPLICATION

This application is a continuous application of Nonprovisional patent application Ser. No. 17/058,432, which is a 35 U.S.C. § 371 national phase application of International Application Serial No. PCT/CN2018/089229, filed on May 31, 2018. The entire content of which is incorporated by reference herein.

BACKGROUND OF THE INVENTION

1. Field of the Invention

The present invention relates to a pharmaceutical composition of a mung bean hull extract and the extraction method thereof, and particularly relates to a pharmaceutical composition of a mung bean hull extract with antiviral effect, and the extraction method and applications thereof.

2. Description of the Prior Arts

According to *Compendium of Materia Medica*, mung beans are mainly used for detumescence and keeping the adverse qi flowing downward, clearing heat, removing toxic substances, treating erysipelas, inducing diuresis, quenching one's thirst, tonifying intestines and stomach, improving eyesight when used as pillow filling, treating headache and migraine, invigorating qi, harmonizing the five viscera, calming, acting on the twelve meridians, moistening skin, and removing toxic substances which come from plants, minerals and arsenic. Mung beans are a non-toxic cold-natured food with sweet flavor, which not only can be used for clearing heat, relieving summer heat, inducing diuresis for detumescence, moistening throat, quenching one's thirst, improving eyesight and lowering blood pressure, but also can be used to treat sunstroke and laryngopharyngitis. Therefore, mung beans are popular summer refreshment for the public.

Mung beans and their hulls and sprouts have different functions. Mung beans can be used for detumescence, regulating qi-flowing, clearing heat, removing toxic substances, tonifying intestines and stomach, treating common cold and headache, and regular consumption of mung beans can invigorate qi, harmonize the five viscera, and regulate the twelve meridians. Mung bean hulls are a non-toxic cold-natured food with sweet flavor, which can be used to remove heat-toxin and treat headache and migraine. Mung bean sprouts are a food with insipid nature and sweet flavor, which can be used to dissipate the effects of alcohol, remove heat-toxin, and regulate triple burner. Mung bean pods can be used to treat long term bloody diarrhea. Modern researches have proven that mung beans are very nutritious, and their protein content is higher than rice. Mung beans have rich carbohydrates, less fat, and they also have proteins, calcium, phosphorus, iron, carotene and the like. Regular consumption of mung bean soup in summer can prevent sunstroke, and skin ulcer and furuncles resulted from heat-toxin, and it is also helpful for nephritis, diabetes mellitus, hypertension, arteriosclerosis, gastroenteritis, laryngopharyngitis and the like.

Mung beans comprise about 20% to 24% proteins, mainly globulin and albumin, which are the main forms of protein stored therein. Mung beans have high protein content and are rich in many essential amino acids; however, mung beans are relatively deficient in threonine, sulfur-containing amino acids, lysine and tryptophan. Mung beans are not easy to digest for economic animals, so it is difficult to apply them to economic animals (Randhir and Shetty, 2007). Currently, there is hardly any research regarding the nutritious ingredients comprised in mung bean hulls.

Virus is an organism smaller than bacteria, which only can be seen under an electron microscope. Nowadays, no effective antiviral agent is found in the pharmaceutical industry, and humans or animals fight against virus infection through their own immunity. Common virus infection comprises enterovirus, human immunodeficiency virus, hepatitis viruses, poliomyelitis, influenza, upper respiratory tract infection and the like. They have strong spreading capability, and usually cause epidemic outbreaks. Regarding influenza (also known as "the flu"), influenza virus infects humans or animals, and results in serious threats to public health and safety and economic loss. A solution is desperately needed.

In Western medicine, there is no effective treatment strategy for virus infection, and the research and development of new drugs is a slow process. Therefore, we combine the knowledge from traditional Chinese medicine and the chemical and biological technologies to promote the value of traditional medicine applications. However, the quality of plant-based raw materials is dramatically fluctuating, and the utilization of plant-based materials is relatively difficult. For example, the raw materials of the plant-based feed additives come from nature, and the ingredients comprised therein change because of several factors, such as the environment and climate of the place of production, which may decide the effect of the product. A solution for this issue is also desperately needed.

SUMMARY OF THE INVENTION

The present invention relates to an antiviral pharmaceutical composition, which is a mixture obtained by: soaking and extracting a raw material of mung bean hulls with a C1 to C6 alcohol in an amount of 5 to 15 times volume (v/w) by ultrasonication after primary extraction; and concentrating and drying.

Preferably, in the present invention, the raw material of mung bean hulls is originated from products named VIVA® (manufactured by King's Ground Biotech Co., Ltd).

Preferably, in the present invention, 50%, 75%, 95% ethanol or methanol is used in an amount of 10 times volume of the raw material (v/w) in the alcohol extracting step.

Preferably, in the present invention, the alcohol extracting is processed by ultrasonic vibration: vibrating and extracting at room temperature for 1 hour; and removing solid residues to obtain an alcohol-extracted solution of mung bean hulls.

Preferably, in the present invention, the alcohol-extracted solution of mung bean hulls is further dried at 50° C. to 60° C. to obtain an alcohol extract of mung bean hulls.

Preferably, in the present invention, the alcohol extract of mung bean hulls comprises about 2 percent by weight (wt %) to 7 wt % of vitexin, or about 2 wt % to 7 wt % of isovitexin, or a combination thereof.

Preferably, in the present invention, the alcohol extract of mung bean hulls can inhibit virus-induced cytopathic effect, in which the virus preferably comprises Orthomyxoviridae (such as influenza virus, avian influenza virus), Paramyxoviridae (such as Newcastle disease virus), herpesvirus or reovirus.

Preferably, in the present invention, the alcohol extract of mung bean hulls can reduce HA (hemagglutination assay) titer of virus in red blood cells, and the virus preferably comprises Orthomyxoviridae (such as influenza virus, avian influenza virus), Paramyxoviridae (such as Newcastle disease virus), herpesvirus or reovirus.

Preferably, in the present invention, the alcohol extract of mung bean hulls achieves antiviral effect by inhibiting α-glucosidase (alpha-glucosidase).

Preferably, in the present invention, the alcohol extract of mung bean hulls achieves antiviral effect by inhibiting neuraminidase, in which the virus preferably comprises Orthomyxoviridae (such as influenza virus, avian influenza virus), Paramyxoviridae (such as Newcastle disease virus), herpesvirus or reovirus.

Preferably, in the present invention, the alcohol extract of mung bean hulls inhibits virus, in which the virus comprises Orthomyxoviridae (such as influenza virus, avian influenza virus), Paramyxoviridae (such as Newcastle disease virus), herpesvirus or reovirus.

The present invention also relates to a method for extracting the pharmaceutical composition of an antiviral mung bean hull extract, comprising: (1) providing a raw material of mung bean hulls; (2) soaking the raw material of mung bean hulls in a C1 to C6 alcohol in an amount of 5 to 15 times volume (v/w) for extraction, to obtain a soaking solution; (3) filtering the soaking solution to obtain an alcohol-extracted solution, and concentrating and drying the alcohol-extracted solution; and (4) obtaining an alcohol extract of mung bean hulls.

Preferably, in the present invention, the raw material of mung bean hulls is originated from products named VIVA®.

Preferably, in the present invention, 50%, 75%, 95% ethanol or methanol is used in an amount of 10 times volume of the raw material (v/w) in the alcohol extracting step.

Preferably, in the present invention, the alcohol extracting is processed by ultrasonic vibration: vibrating and extracting at room temperature for 1 hour; and removing solid residues to obtain an alcohol-extracted solution of mung bean hulls.

Preferably, in the present invention, the alcohol-extracted solution of mung bean hulls is further dried at 50° C. to 60° C. to obtain an alcohol extract of mung bean hulls.

The present invention also relates to a feed additive prepared by the above-mentioned extraction method.

DETAILED DESCRIPTION OF THE PREFERRED EMBODIMENTS

Figure 1A:
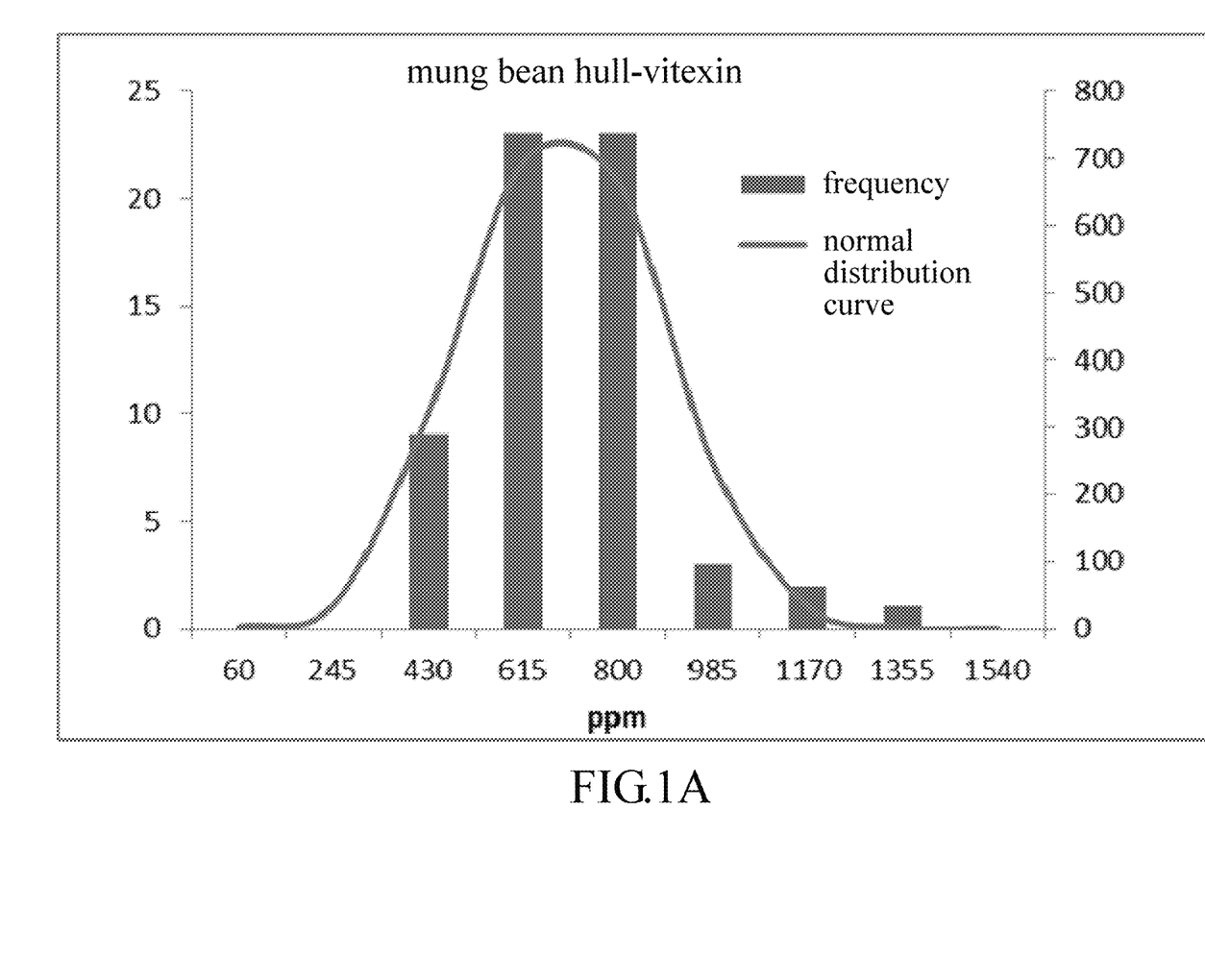
FIGS. 1A to 1D show the normal distribution of vitexin and isovitexin obtained by the extraction method of the present invention.
Figure 1B:
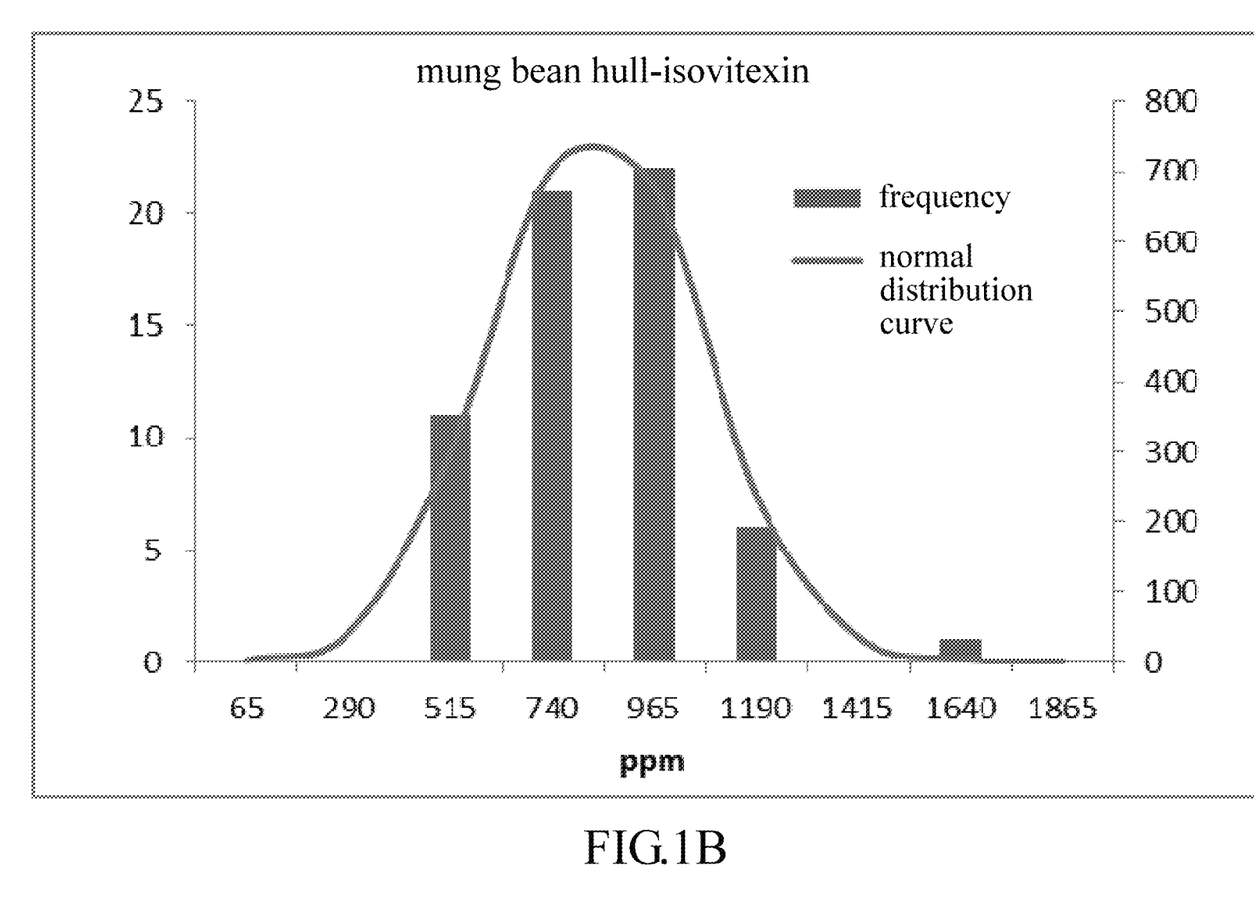
Figure 1C:
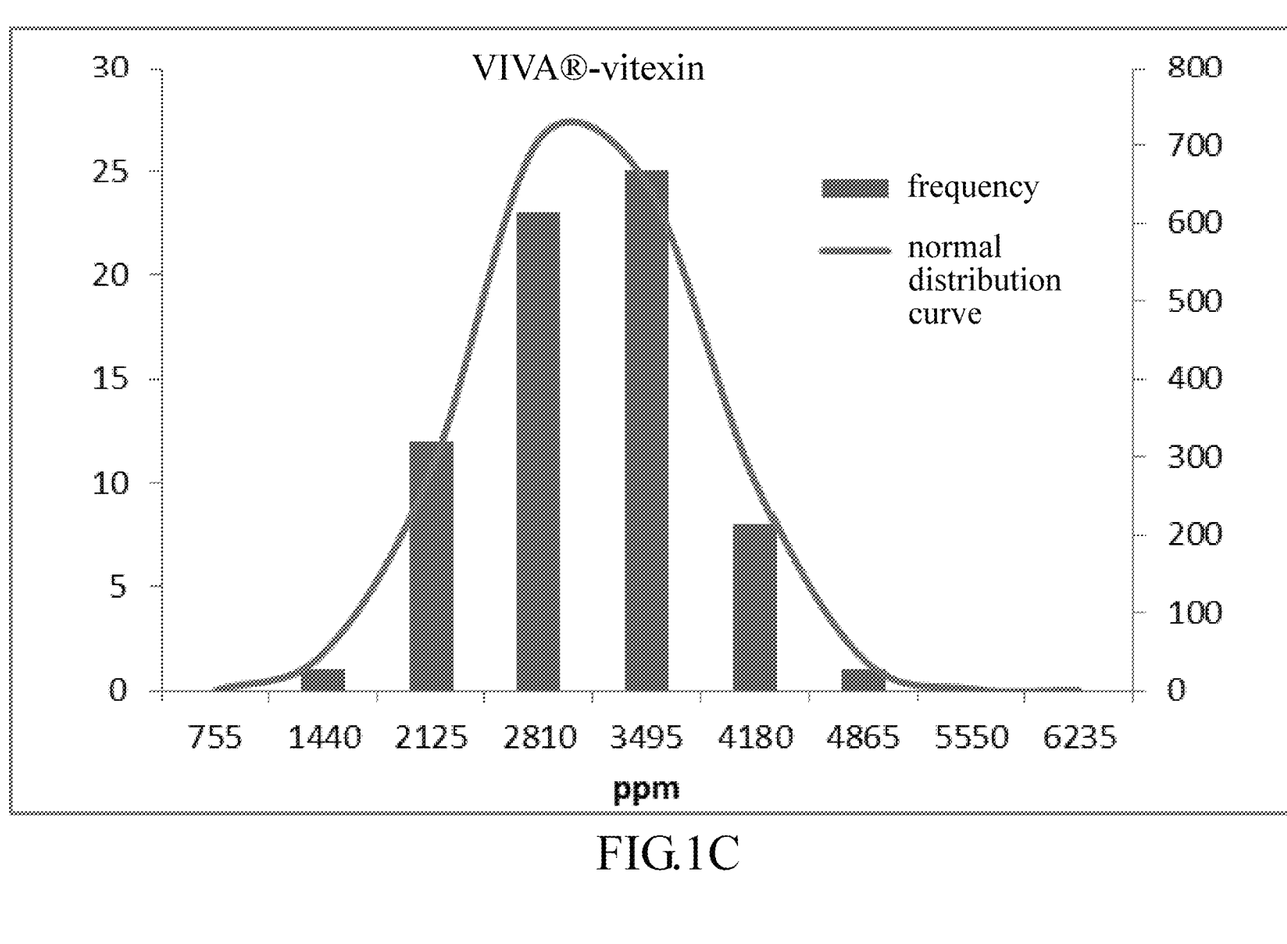
Figure 1D:
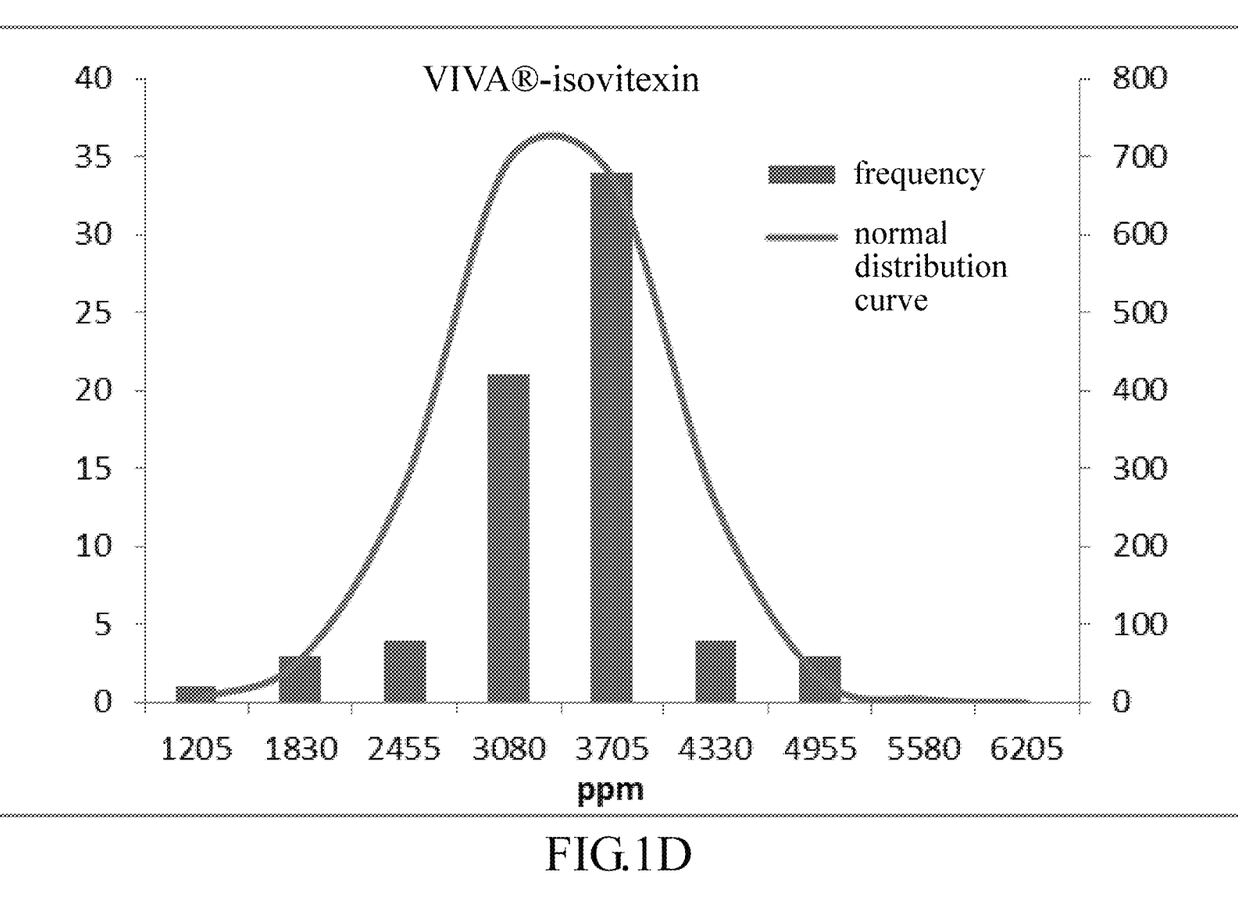
Figure 2:
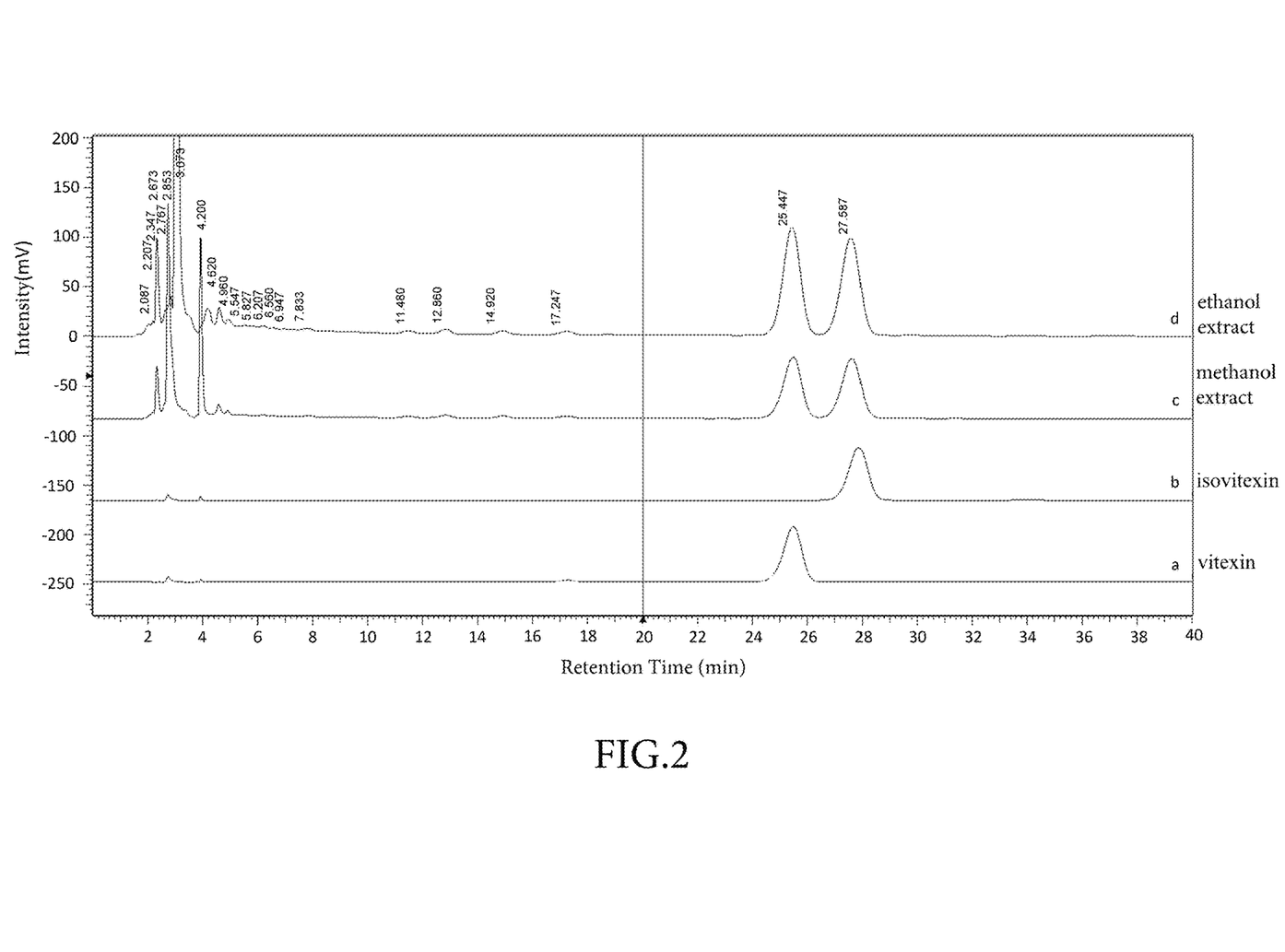
FIG. 2 shows the chromatograms of the standard substances 25 ppm vitexin and 25 ppm isovitexin, and the methanol extract of VIVA® and ethanol extract of VIVA® of the present invention.

The present invention relates to a mung bean hull extract with antiviral effect, which is treated by the process of King's Ground Biotech Co., Ltd to obtain a product named VIVA®. In FIGS. 1A to 1D, the normal distribution curves show that all mung bean hulls in different batches and from different sources can provide a mixture comprising a large amount of vitexin and isovitexin. From the chromatograms of the standard substances 25 ppm vitexin and 25 ppm isovitexin, and the methanol extract of VIVA® and the ethanol extract of VIVA®, as shown in FIG. 2, it is found that the extraction method of the present invention can overcome the problem of changes caused by several factors, such as environment and climate of the place of production which usually happen to general natural products, and the active ingredients can be identified and quantified to achieve quality stabilization, so it can be further applied as a feed additive or a food additive. Therefore, the present invention also relates to a feed additive which promotes the health of animals.

Further, the present invention relates to a mung bean hull extract which can reduce virus cytopathic effect and HA titer, in which the virus preferably comprises Orthomyxoviridae (such as influenza virus, avian influenza virus), Paramyxoviridae (such as Newcastle disease virus), herpesvirus or reovirus, and the extract obtained by the extraction method disclosed by the present invention mainly comprises active ingredients, vitexin and isovitexin. The two active ingredients have the ability for inhibiting α-glucosidase and neuraminidase, which results in antiviral effect.

The mung bean hull extract of the present invention is preferably extracted by a C1 to C6 alcohol, which comprises, but not limited to, 50%, 75%, 95% ethanol, methanol or any other alcohols. It is preferably to be extracted by ethanol, and the results by extracting with ethanol at different concentrations show that they all comprise a specific amount of vitexin and isovitexin. For convenience of demonstrating the best example of the present invention, the alcohol extracts are hereinafter referred to as ethanol extract or EE.

Example 1: Extraction of Active Ingredients of Mung Bean Hull Extract

Figure 3:
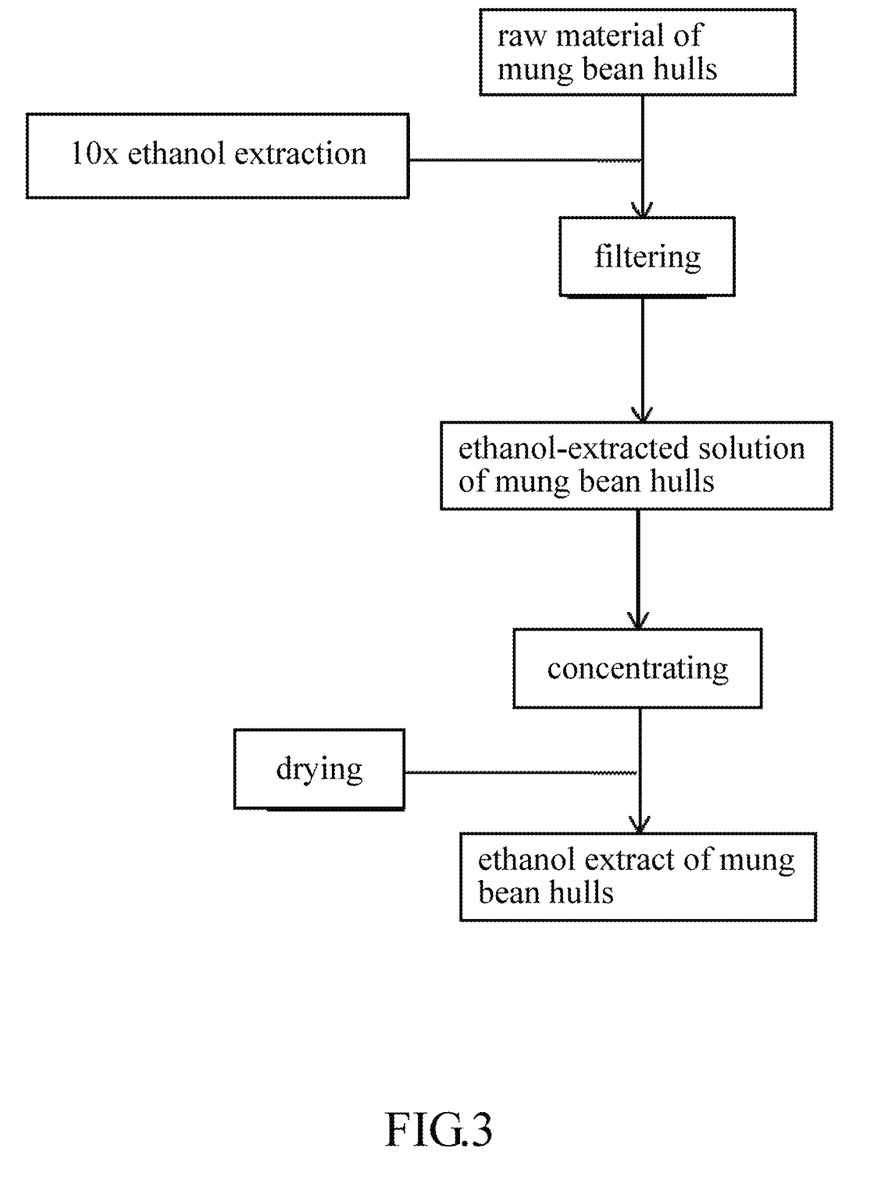
FIG. 3 is the flow chart of the extraction process of the present invention.

As shown in FIG. 3, with the preparation process of King's Ground Biotech, a raw material of mung bean hulls was provided, scheduled for production, blended, physically, chemically and biologically treated, measured and packaged to obtain the product, named VIVA®, which could be used as an animal feed additive or an additive for other foods. In the small scale production in laboratory, the unit of weight was 50 grams (g). 50 g of the obtained animal feed additive was added into 95% ethanol in an amount of 10 times volume, i.e. 500 milliliters (ml), and extracted by ultrasonication. It was vibrated at room temperature for 1 hour, and solid residues were removed by coarse filtration to obtain the ethanol-extracted solution of mung bean hulls of the present invention. The volume at this stage was about 350 ml to 380 ml, with a recovery rate of about 70% to 80%. After concentration under reduced pressure, an extractum of 20 g to 25 g could be obtained, which was about 40% to 50% of the raw material by weight. The extractum was dried at 50° C. to 60° C. to remove the remaining water and obtain 10 g to 15 g of the ethanol extract of mung bean hulls, which was about 20% to 30% of the raw material by weight (w/w).

Example 2: Active Ingredient Test of Ethanol Extract of Mung Bean Hulls

Figure 4:
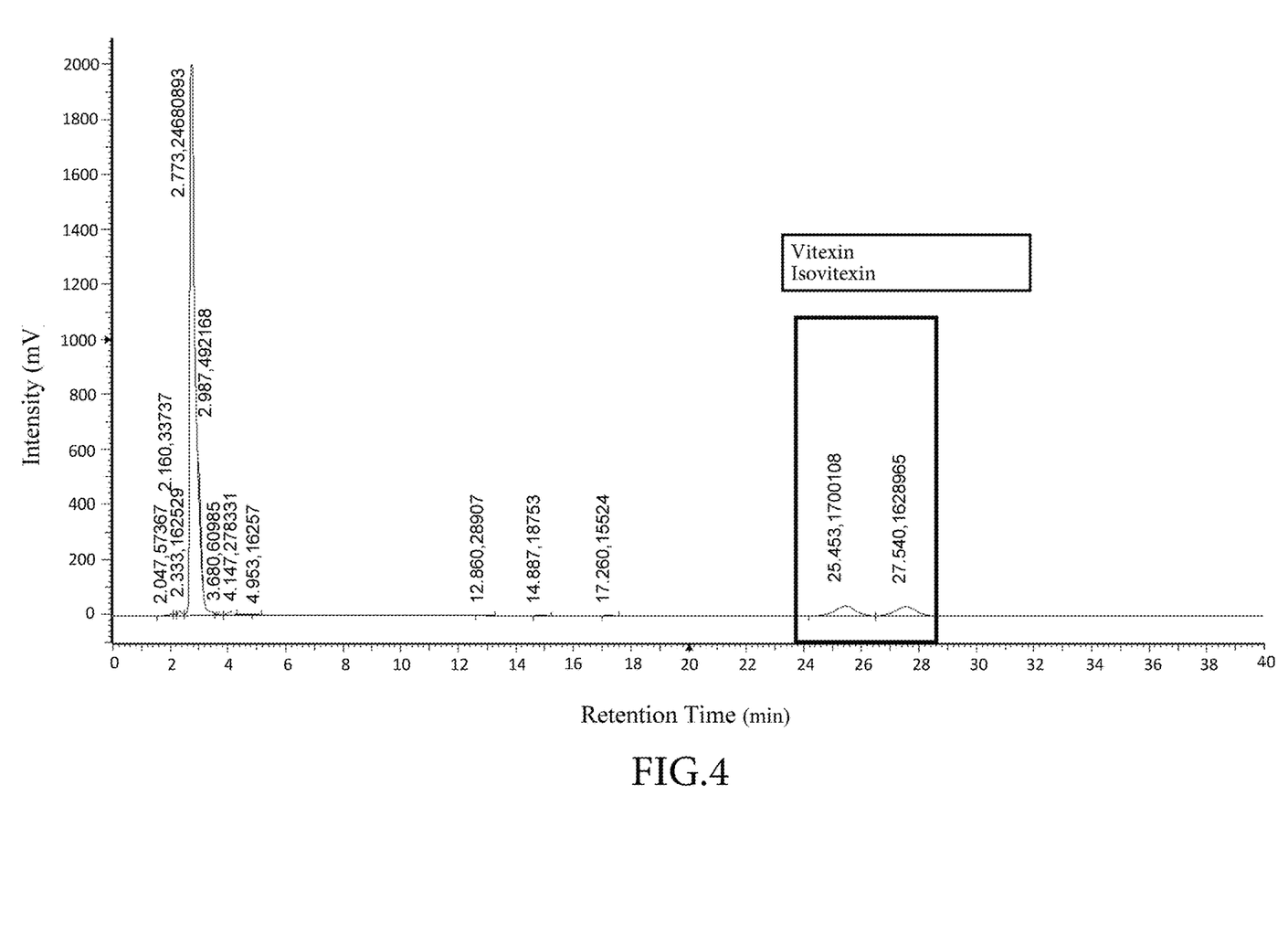
FIG. 4 shows the HPLC column chromatogram of the extract of the present invention.

The ethanol extract of mung bean hulls obtained from Example 1 was dissolved in DMSO. 1.4 g of the ethanol extract of mung bean hulls was dissolved in 14 ml of DMSO, then diluted 100 times with methanol, and primarily analyzed by HPLC for ingredient analysis. As shown in FIG. 4, after comparison with the standard substances, it was confirmed that the two peaks produced during the period of retention time between about 25 minutes and 30 minutes were vitexin and isovitexin, respectively. After calculation, it was found that the absolute amount of vitexin was 31.015 milligrams (mg) (2.22% of the ethanol extract), and the absolute amount of isovitexin was 33.893 mg (2.42% of the ethanol extract).

From the prior art, it was known that vitexin and isovitexin had ability of inhibiting $\alpha$-glucosidase and neuraminidase, so they could inhibit virus activity. Currently, pure vitexin and isovitexin or their standard substances are expensive, costing several to tens of thousands New Taiwan dollar (NTD) for 10 mg, depending on their purity, in which the price of isovitexin is higher. Because of the price issue, their utilities and applications are limited.

Example 3: Cytotoxicity Test

Since the developed drugs had to meet the safety requirements, and their concentration in use could not result in toxicity, the cytotoxicity test of the ethanol extract of the present invention was further tested. DMSO was used as the blank control. With DMSO at the concentration of 1%, the cells exhibited no difference in growth and morphology, which meant no toxicity.

Figure 5:
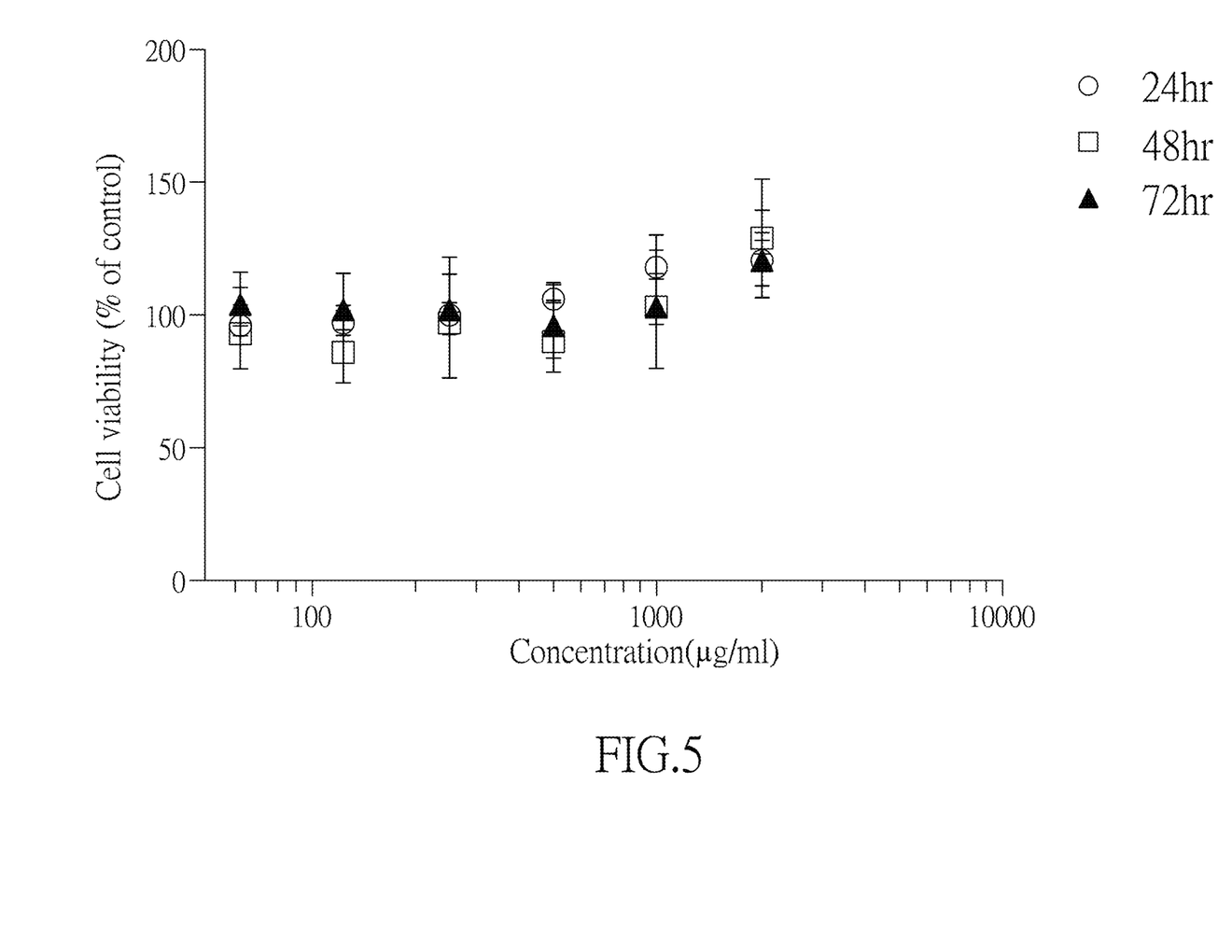
FIG. 5 shows the cytotoxicity test results of the ethanol extract of mung bean hulls of the present invention.

The cell line used was MDCK cells (canine kidney epithelial cells), which is a common cell line target used in tests for exploring influenza. The cell culture medium used was DMEM with 10% FBS serum and 1% PSA antibiotic mixture. 1.4 g of the ethanol extract of mung bean hulls was dissolved in 5.6 ml of DMSO to obtain a highly concentrated 250 milligrams/millimeter (mg/ml) storage solution of the ethanol extract of mung bean hulls, and then diluted by DMSO into working concentrations of 62.5, 125, 250, 500, 1000, 2000 micrograms/milliliter (μg/ml) respectively. Cells were seeded in petri dishes and grown for 24 hours, then the ethanol extract of mung bean hulls to be tested was added. After 24, 48, 72 hours, cell viability was respectively analyzed (MTT assay). As shown in FIG. 5, the test was held by MDCK cells, and the ethanol extract of mung bean hulls having a concentration of 2000 (μg/ml) or lower showed no cytotoxicity, which meant that it was excellently safe.

Example 4: Antiviral Test-Ethanol Extract of Mung Bean Hulls

Inhibits Cytopathic Effect (CPE) of Influenza Virus Influenza virus particles infected cells and then killed the host cells, which produced cytopathic effect (CPE). Therefore, when the cytopathic effect was inhibited, it was deemed as antiviral effect.

In the present invention, MDCK cells (canine kidney epithelial cells) were used as the target of the test. The virus strain used was PR8 (H1N1), and the ethanol extract of mung bean hulls was at a concentration of 0, 125, 2000 (μg/ml), in which 0 μg/ml was used as the DMSO blank control. In this test, the cell line was seeded first. After 24 hours, the MDCK cells were pre-treated with the ethanol extract of mung bean hulls at different concentrations for 1 hour, and the PR8 virus strain was pre-treated with the ethanol extract of mung bean hulls at different concentrations for 1 hour. After that, the virus pre-treated by the ethanol extract of mung bean hulls and the cell line pre-treated with the ethanol extract of mung bean hulls were co-cultured for infection. After 1 hour of infection, the virus solution was removed and the ethanol-extracted solution of mung bean hulls was added. 24 hours later, the CPE test results were observed.

Figure 6:
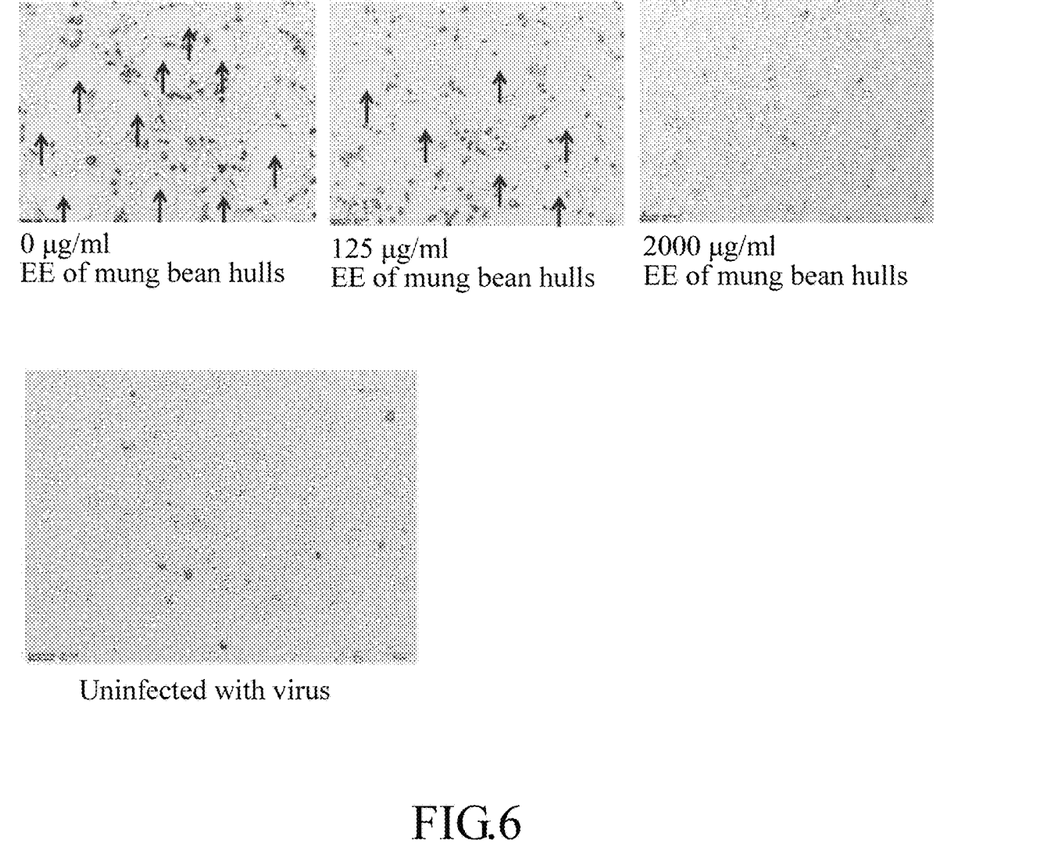
FIG. 6 shows the cytopathic effect test results of the ethanol extract of mung bean hulls of the present invention.

As shown in FIG. 6, the arrows indicated the place cytopathic effect (CPE) occurred. With the ethanol extract of mung bean hulls of the present invention, the occurrence of cytopathic effect can be reduced. At the concentration of 2000 μg/ml, no cytopathic effect was observed, and the morphology of cells under the microscope was normal.

Example 5: Antiviral Test-Ethanol Extract of Mung Bean Hulls Reduces HA Titer of Influenza Virus in Cells The hemagglutinin on the surface of influenza virus could combine with receptors on red blood cells. When the titer of virus was high enough, hemagglutination of red blood cells occurred. Therefore, hemagglutination of red blood cells could be utilized as a method for testing virus titer. It was also called hemagglutination assay (HA).

The cell line and the concentrations of the ethanol extract of mung bean hulls of the present invention were the same as described in Example 4. In this test, the cell line was seeded first. After 24 hours, the MDCK cells were pre-treated with the ethanol extract of mung bean hulls at different concentrations for 1 hour, and the PR8 virus strain was pre-treated with the ethanol extract of mung bean hulls at different concentrations for 1 hour. After that, the virus pre-treated by the ethanol extract of mung bean hulls and the cell line pre-treated with the ethanol extract of mung bean hulls were co-cultured for infection. After 1 hour of infection, the virus was removed and the ethanol-extracted solution of mung bean hulls was added. 24 hours later, cell culture medium was collected for the HA titer test.

Figure 7:
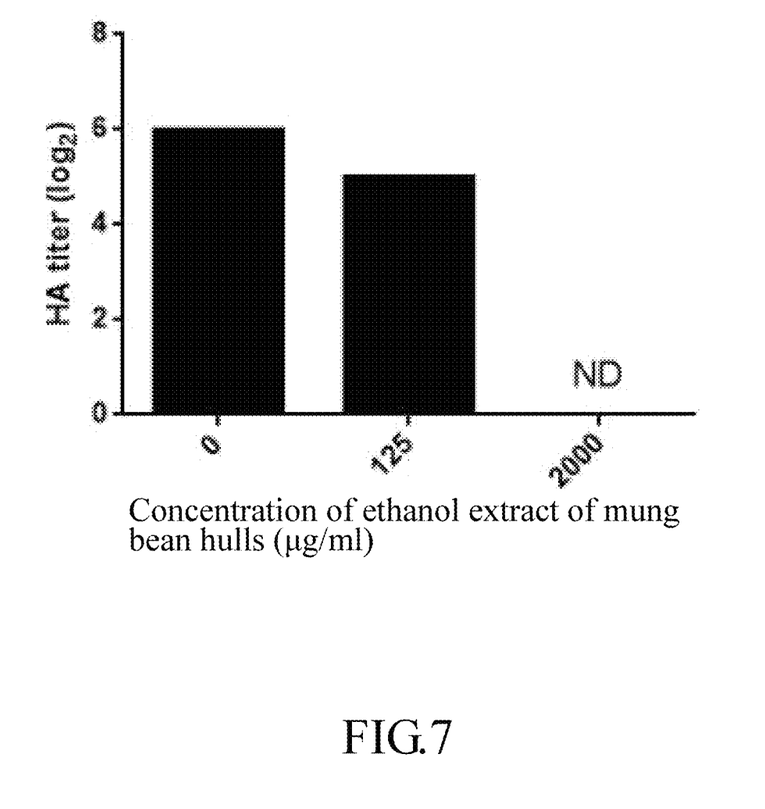
FIG. 7 shows the test results that the ethanol extract of mung bean hulls of the present invention reduces HA titer of virus in cells.

As shown in FIG. 7, the results showed that the HA titer of cells could not be detected when the ethanol extract of mung bean hulls of the present invention had a concentration of 2000 μg/ml. Therefore, it was known that the ethanol extract of mung bean hulls of the present invention can reduce the HA titer of influenza virus in MDCK cells.

Example 6: Ability Test of Inhibiting $\alpha$-Glucosidase for Ethanol Extract of Mung Bean Hulls 0.8 microliter (μL) of the ethanol extract of mung bean hulls (with a concentration of 20 mg/mL, 10 mg/mL, 5 mg/mL, 2.5 mg/mL, 1.25 mg/mL, 0.625 mg/mL, 0 mg/mL, dissolved in DMSO) was provided. The dissolved ethanol extract of mung bean hulls was mixed with 69.2 μL of phosphate buffer (100 millimolar (mM), pH 6.8) and 10 μL of α-glucosidase (1 unit per milliliter (U/mL), Sigma), and placed in a 37° C. incubator for culturing for 15 minutes.

Figure 8:
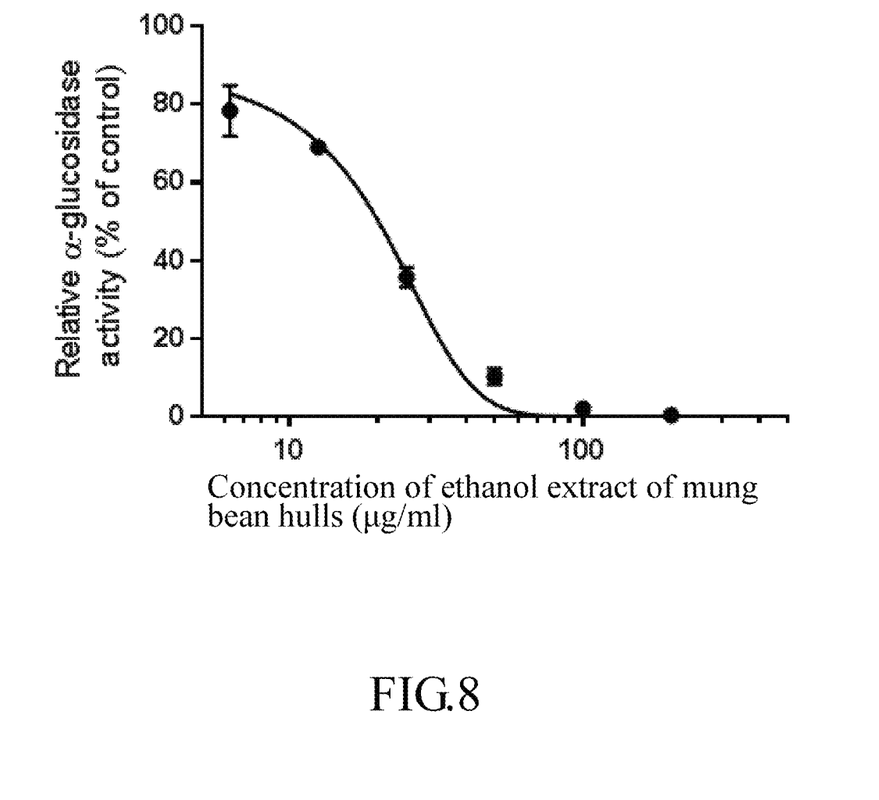
FIG. 8 shows the results of the ability test of inhibiting α-glucosidase for the alcohol extract of mung bean hulls of the present invention.
Figure 9A:
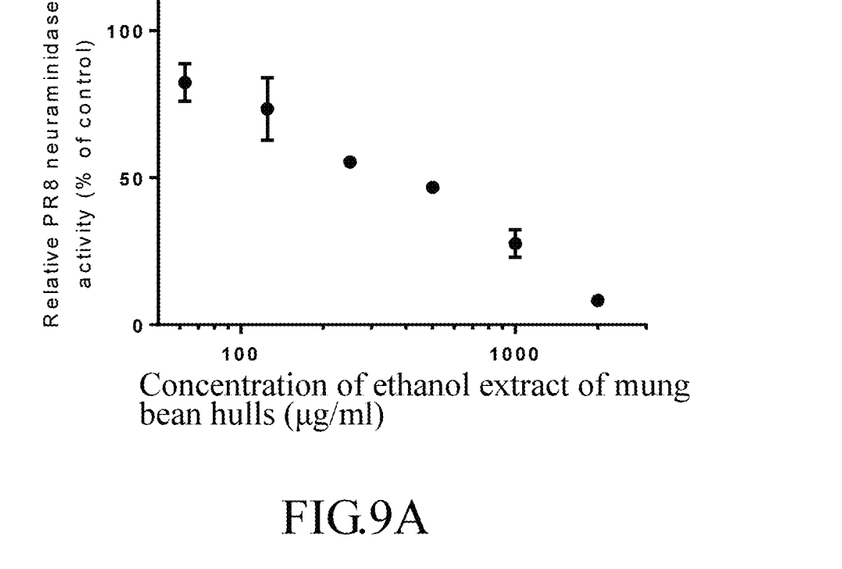
FIGS. 9A to 9D show the results of the ability test of inhibiting neuraminidase for the alcohol extract of mung bean hulls of the present invention.
Figure 9B:
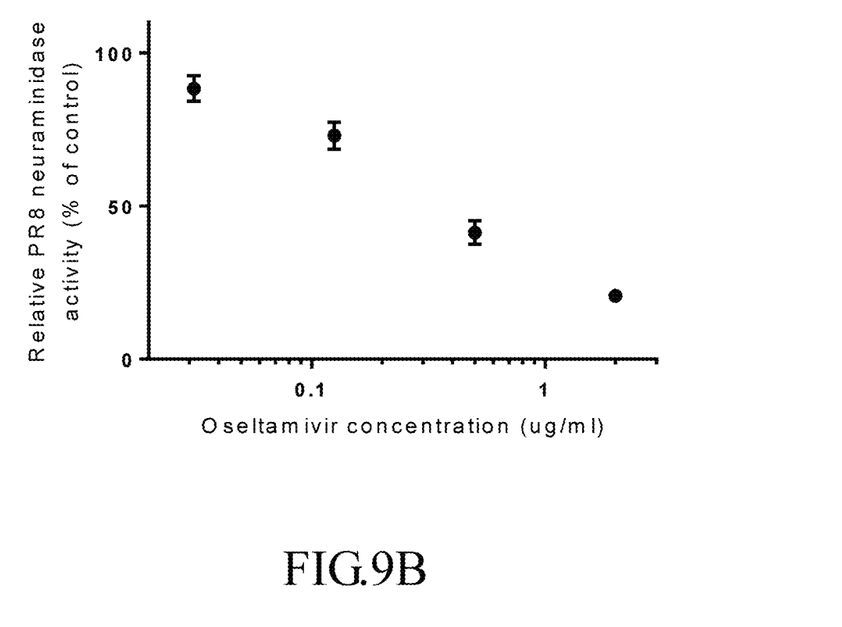
Figure 9C:
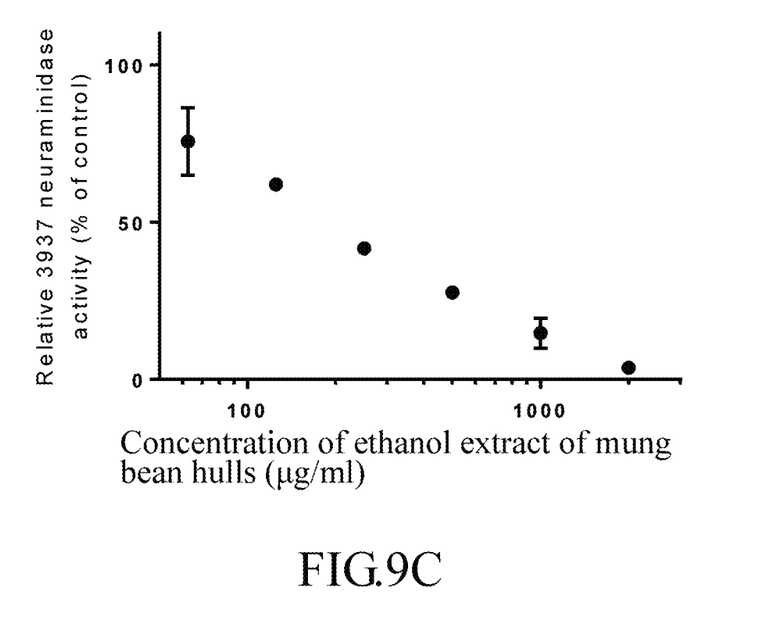
Figure 9D:
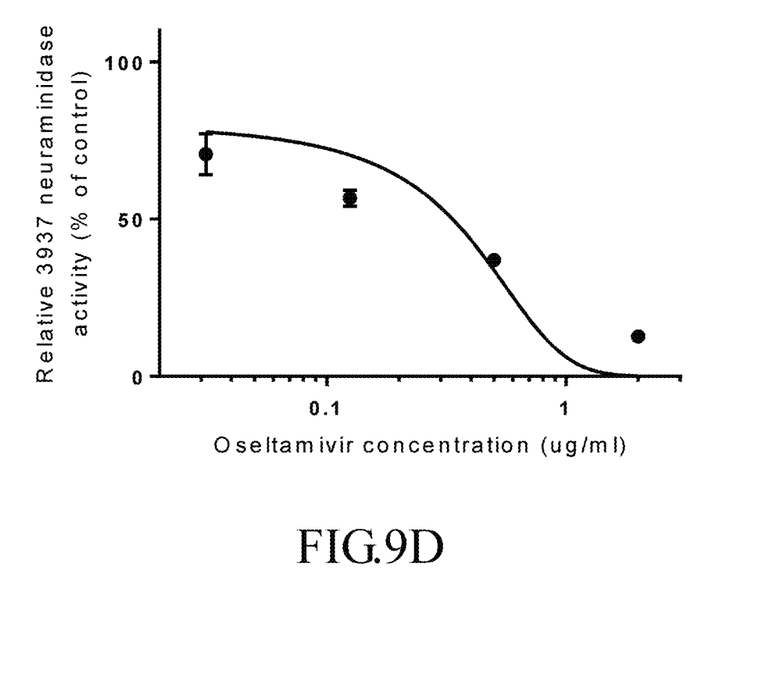

After culturing, 20 μL of p-nitrophenyl-α-d-glucopyranoside (5 mM, Sigma) was added as a substrate into the culture solution, and cultured in a 37° C. incubator for 20 minutes. After that, 50 μL of $Na_2CO_3$ (0.1 M) was added to terminate the reaction, and the absorbance was measured by a spectrophotometer at 450 nm and the measurement results were recorded. As shown in FIG. 8, the results showed that the ethanol extract of mung bean hulls could reduce the activity of α-glucosidase in a dose-dependent manner, with $IC_{50}$ of 20.07±0.9 μg/mL, which was lower than the $IC_{50}$ values of vitexin and isovitexin disclosed in references, 23.9 μg/mL and 46.9 μg/mL, respectively. This result demonstrated that the ethanol extract of mung bean hulls of the present invention had an excellent ability for inhibiting α-glucosidase activity, so it also exhibited antiviral ability and potential. Preferably, the virus might come from the family of virus which needed α-glucosidase, such as Orthomyxoviridae (such as influenza virus, avian influenza virus), Paramyxoviridae (such as Newcastle disease virus), herpesvirus or reovirus, and the like.

Example 7: Ability Test of Inhibiting Neuraminidase for Ethanol Extract of Mung Bean Hulls Neuraminidase was a necessary enzyme that enables influenza virus particles to be released from host cells. Therefore, inhibition of neuraminidase activity was a strategy for treating influenza. In fact, neuraminidase inhibitors have been clinically used to treat influenza. In the present invention, we used the neuraminidases obtained from mammalian influenza virus H1N1 (PR8) and avian influenza virus H6N1 (3937) for the neuraminidase activity inhibiting test of the ethanol extract of mung bean hulls of the present invention.

1 μL of the ethanol extract of mung bean hulls (with a concentration of 200 mg/ml, 50 mg/ml, 12.5 mg/ml, 3.125 mg/ml, 0 mg/ml, dissolved in DMSO) was provided, and mixed with 25 μL of virus (comprising 128× diluted 3937 virus particles and 8× diluted PR8 virus particles), and the volume was adjusted by 1× analyzing buffer (33 mM MES (2-(N-morpholino) ethanesulfonic acid or 4-morpholineethanesulfonic acid, SIGMA, M3671), 20 mM $CaCl_2$), pH 6.5) to 50 μL, and placed in a 37° C. incubator for culturing for 20 minutes. After that, 50 μL of fluorogenic substrate (50 micromolar (μM) 4-methylumbelliferyl-N-acetylneuraminic acid, Sigma) was added and co-cultured in a 37° C. incubator for 60 minutes. Finally, 100 μL of 0.2 M $Na_2CO_3$ was added to terminate the reaction. Fluorescence was measured with an excitation wavelength of 355 nm and an emission wavelength of 460 nm. Relative fluorescence unit (RFU) was obtained based on the background, and inhibition rate (IR) was calculated by the following equation: IR (%)=(1−RFU sample/RFU DMSO)×100%.

Similar to oseltamivir, as shown in FIGS. 9A to 9D, the ethanol extract of mung bean hulls had the ability for inhibiting neuraminidase of mammalian influenza virus or avian influenza virus in a dose-dependent manner. From the results, it was clear that the ethanol extract of mung bean hulls of the present invention had excellent ability for inhibiting neuraminidase activity, so it exhibited antiviral ability and potential. Preferably, the virus could be mammalian influenza virus or avian influenza virus.

Examples of the present invention showed that the ethanol extract of mung bean hulls of the present invention has antiviral ability, and the antiviral effect may be achieved through the mechanism of inhibiting α-glucosidase and neuraminidase of the virus. Therefore, it can be used against the virus having α-glucosidase and/or neuraminidase. Meanwhile, the ethanol extract of mung bean hulls of the present invention shows no cytotoxicity in in vitro tests, which is a safe and good antiviral product.

The extraction method and the resulting extract provided by the present invention have excellent cost advantages, including low-cost raw material source, high yield of vitexin and isovitexin or a combination thereof, good recovery, and simple extraction method; therefore, it is advantageous for applications in the industries, and valuable for further development and protection.

What is claimed is:

1. A method for treating influenza virus, avian influenza virus, Newcastle disease virus, herpesvirus or reovirus in a mammal or avian species in need thereof consisting essentially of administering to said mammal or avian species in need thereof an ethanol or methanol extract of mung bean hulls, the ethanol or methanol extract of mung bean hulls which are obtained by:
   a) soaking, vibrating and extracting raw mung bean hulls with ethanol or methanol in an amount 10 times volume (v/w) of the mung bean hulls by ultrasonic vibration at room temperature for 1 hour to produce solid residues;
   b) removing the solid residues to obtain a methanol or ethanol extracted solution of mung bean hulls, wherein the methanol or ethanol is at least 50% ethanol or methanol; and
   c) concentrating and drying the extracted mung bean hulls at 50° C. to 60° C. which when administered to the mammal or avian species in need thereof effectively treats the influenza virus, avian influenza virus, Newcastle disease virus, herpesvirus or reovirus in the mammal or avian species in need thereof; wherein the methanol or ethanol extract of mung bean hulls consists essentially of about 2 wt. % to 2.22 wt. % of vitexin, and about 2 wt. % to 2.42 wt. % of isovitexin.

2. The method as claimed in claim 1, wherein the methanol or ethanol extract of mung bean hulls inhibits a virus-induced cytopathic effect.

3. The method as claimed in claim 1, wherein the methanol or ethanol extract of mung bean hulls is administered to the mammal or avian species in need thereof in a feed consisting essentially of the methanol or ethanol extract of mung bean hulls.

* * * * *